United States Patent [19]

van Zelderen

[11] Patent Number: Plant 6,661

[45] Date of Patent: Mar. 14, 1989

[54] ALSTROEMERIA NAMED ZELBLANCA

[76] Inventor: Gerard J. van Zelderen, Achterweg 34-36, 1424 PR De Kwakel, Netherlands

[21] Appl. No.: 100,716

[22] Filed: Sep. 24, 1987

[51] Int. Cl.[4] ..... A01H 5/00

[52] U.S. Cl. ..... Plt./68

[58] Field of Search ..... Plt. 68

*Primary Examiner*—Robert E. Bagwill

*Attorney, Agent, or Firm*—Charles W. Rummler

[57] ABSTRACT

A new and distinct Alstroemeria cultivar particularly distinguished by the substantially overall white color of the outer petals which surround heavily striped inner petals, the upper pair of which have an almost overall coloring of yellow and being accented by dark brown, longitudinally-extending pencil stripes arising from a dark brown base and the lower one of which is substantially white but also bears the longitudinally-extending brown stripes. This new plant is further distinguished by its continued and profuse year around blooming habit, the very large size of its generally white flowers, its vigorous, upright growth habit, and by the excellent lasting quality of its blooms both on the plant and as cut flowers.

1 Drawing Sheet

BACKGROUND OF THE NEW PLANT

My new Alstroemeria cultivar originated as a seedling of unknown parentage discovered by me among my collection of Alstroemeria varieties maintained in greenhouse at De Kwakel, Holland, for developmental and breeding purposes. This particular seedling caught my attention because of the substantially all white appearance of its flowers clustered in an umbel formation appearing at the top of a relatively tall flowering stem. I propagated this seedling discovery by root division through several successive generations and found that the novel and distinctive features of the discovery plant would hold true from generation to generation and appeared to be firmly fixed. Propagation of this new seedling for commercial purposes is being carried on at De Kwakel, Holland, with very favorable results.

DESCRIPTION OF THE DRAWING

This new Alstroemeria cultivar is illustrated by the accompanying photographic drawing, which shows a number of the blooms in face view appearing in an umbel cluster, the drawing illustrating the flower form and coloration with a color rendition that is as nearly true to those specified herein as is reasonably possible to obtain by conventional photographic procedures.

DESCRIPTION OF THE NEW PLANT

The following is a detailed description of my new Alstroemeria cultivar as observed in greenhouse at De Kwatel, Holland, the color designations being according to the R.H.S. Colour Chart of The Royal Horticultural Society of London, England.

THE PLANT

Origin: Seedling.
Parentage: Unknown.
Classification: Alstroemeria hybrid.
Form: Erect bush.
Height: About 205 cm., in average.
  Main stem or cane length.—About 150 to 200 cm., depending upon season.
Growth: Vigorous and upright, and of medium strength.

Root stock: Tuberous, the tubers bearing many buds in the course of the year from which flower stalks appear in various stages of development.
Branching: The flower stalk branches at its top to form an umbel of many flowering stems.
Foliage:
  *Quantity.*—Medium, the number of leaves depending on season.
  *Leaf size.*—Depends upon season.
  *Leaf shape.*—Elliptical with entire margins.
  *Texture.*—Leathery.
  *Color.*—Medium green on both upper and under sides.
  *Rizomes.*—Size: Depending on season. Color: White.

THE BUD

Form: Pear shaped.
Size: Medium.
  *Diameter.*—About 1.5 cm.
  *Length.*—About 4 cm.
Opening rate: Normal.
Sepals:
  *Number.*—Six.
  *Shape.*—Elliptical.
  *Color.*—Near white when flowers begin to open.
Peduncle:
  *Length.*—About 4 to 5 cm.
  *Color.*—Middle green.

THE FLOWER

Blooming habit: Continuous the year around.
Flower size: Very large.
  *Diameter.*—About 8 cm.
  *Depth.*—About 5 cm.
Borne: Singly in the stem of an umbel near the top of a flowering main stem.
Shape: When bloom matures, funnel-like with petal tip curling outward.
Petalage:
  *Number of petals.*—Six.
  *Arrangement.*—Two concentric groups of three with upper petals of inner group mutually contiguous.

*Texture.*—Leathery.

*Appearance*—Shiny.

*Color.*—Outer petals: White, 155 D, with a dark yellow shade at the base. Reverse side — 155 D. Inside petals: Upper pair —Mainly 8 A with 155 D in the outer end margins and with brown lengthwise pencil stripes extending from base to petal tip. The lower one of the inside petals is white with a few pencil stripes.

Peduncle or flower stem:

*Length.*—About 4 to 5 cm.

*Color.*—Middle green.

Discoloration after full bloom: The nectariae of the inner petals turn to brown.

Presistence: The flower petals hang on and dry.

Lasting quality:

*On the plant.*—About twenty-one days.

*As cut flowers.*—About fifteen days.

THE REPRODUCTIVE ORGANS

Stamens:

*Number.*—Six, one opposite each petal.

*Anthers.*—Size: About 0.8 to 1.0 cm. Color: Grey-Green.

*Filaments.*—Length: About 4 cm. Color: Tip — White. Base — Red striped.

*Pollen.*—Color: Yellow.

Pistils:

*Number.*—One.

*Style.*—Length: About 5 cm., varies with age. Color: White with some red stripes.

*Stigma.*—Color: Greenish white.

THE FRUIT

Fertility: The fruit is fertile.

Shape: Capsular.

Color at maturity: Light brown.

I claim:

1. The new and distinctive Alstroemeria cultivar and parts thereof substantially as herein shown and described, characterized by the pure white coloration of the outer petals of its flowers and the end portions only of the upper pair of the inner petals, the principal body portion of the lower one of the inner petals having a distinctive yellow coloration and the upper ones of the inner petals being heavily marked with dark, longitudinally-extending pencil stripes; and by the very large size of the flowers and the vigorous, upright and tall growth habit of the plant.

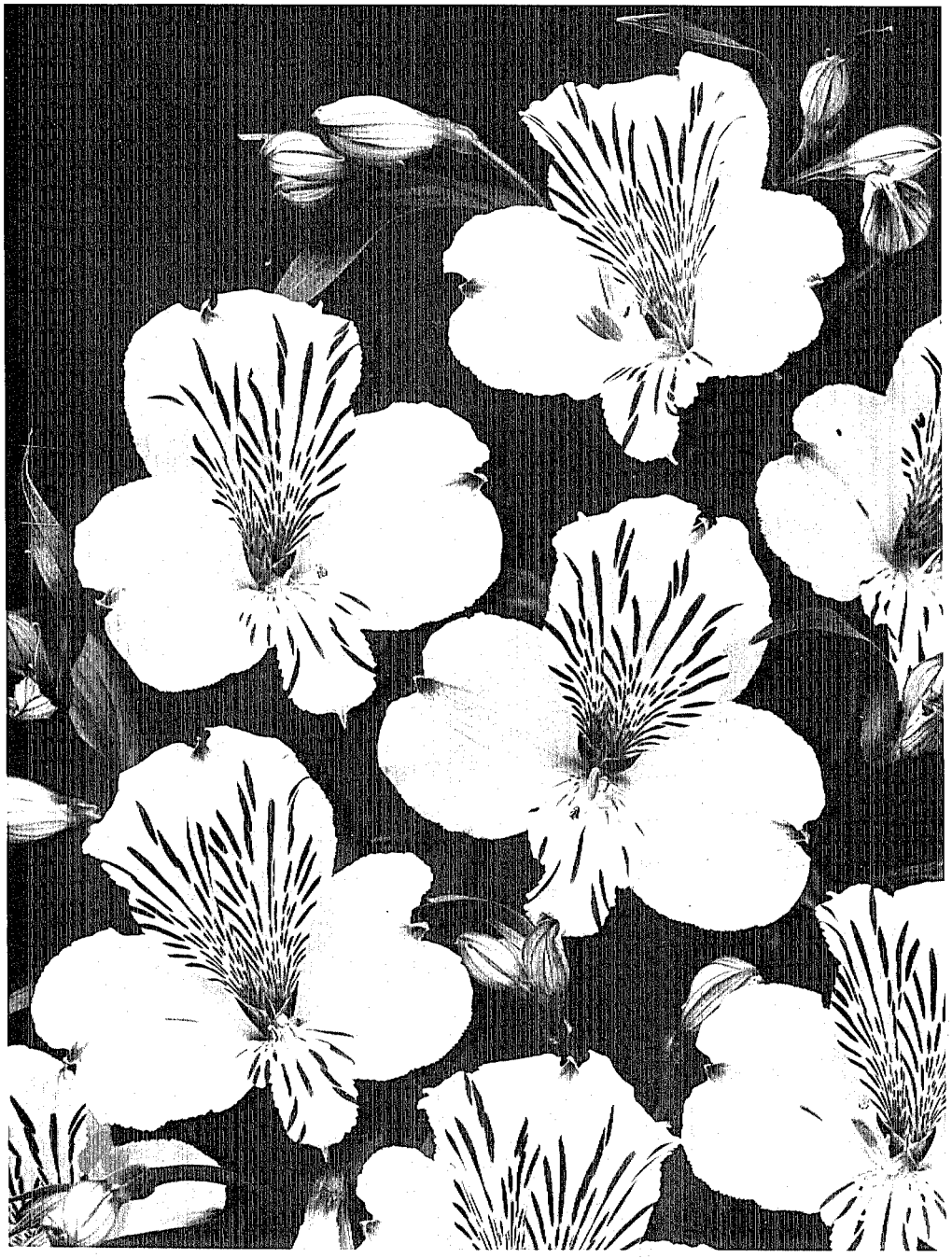

* * * * *